(12) United States Patent
Thadani et al.

(10) Patent No.: US 8,759,541 B2
(45) Date of Patent: Jun. 24, 2014

(54) CHIRAL ACYCLIC DIAMINOCARBENE LIGANDS, PRECURSORS THEREFORE AND THEIR USE IN ORGANIC SYNTHESIS REACTIONS

(76) Inventors: Avinash N. Thadani, Windsor (CA); Rukundo Ntaganda, Windsor (CA); Mira M. Beshai, Stittsville (CA)

( * ) Notice: Subject to any disclaimer, the term of this patent is extended or adjusted under 35 U.S.C. 154(b) by 541 days.

(21) Appl. No.: 13/003,039

(22) PCT Filed: Jul. 7, 2009

(86) PCT No.: PCT/CA2009/000928
§ 371 (c)(1),
(2), (4) Date: Jan. 7, 2011

(87) PCT Pub. No.: WO2010/003226
PCT Pub. Date: Jan. 14, 2010

(65) Prior Publication Data
US 2011/0118475 A1  May 19, 2011

Related U.S. Application Data

(60) Provisional application No. 61/078,985, filed on Jul. 8, 2008.

(51) Int. Cl.
C07D 207/09 (2006.01)
C07D 403/04 (2006.01)

(52) U.S. Cl.
CPC ............ *C07D 207/09* (2013.01); *C07D 403/04* (2013.01)
USPC ............................ 548/518; 548/569; 546/208

(58) Field of Classification Search
None
See application file for complete search history.

(56) References Cited

U.S. PATENT DOCUMENTS 6,888,002 B2  5/2005  Herrmann et al.
2003/0195357 A1  10/2003  Stuer et al.

FOREIGN PATENT DOCUMENTS

WO  WO02/34723  5/2002

OTHER PUBLICATIONS

Alder, R. W.; Allen, P. R.; Murray, M.; Orpen, A. G. Angew. Chem., Int. Ed. 1996, 35, 1121.
Alder, R. W.; Blake, M. E.; Bufali, S.; Butts, C. P.; Orpen, A. G.; Schutz, J.; Williams, S. J. J. Chem. Soc., Perkin Trans. 1 2001, 1586-1593.
Cavallo, L.; Correa A.; Costabile, C; Jacobsen, H. J. Organomet. Chem. 2005, 690, 5407.
Michael Chong, J.; Clarke, I. S.; Koch, I.; Olbach, P. C.; Taylor, N. J. Tetrahedron: Asymmetry 1995, 6, 409-418.
Dhudshia, B.; Thadani, A. N. Chem. Commun. 2006, 668-770.
Frey, G. D.; Herdtweck, E.; Herrmann, W. A. J. Organomet. Chem. 2006, 691, 2465.
Gillingham D. G.; Hoveyda, A. H. Angew. Chem., Int. Ed. 2007, 46, 3860.
Herrmann, W. A.; Schutz, .; Frey, G. D.; Herdtweck, E. Organometallics 2006, 25, 2437.
Iseki, K.; Mizuno, S.; Kuroki, Y.; Kobayashi, Y. Tetrahedron 1999, 55, 977-988.
Kantchev, E. A. B.; O'Brien, C. J.; Organ, M. G. Angew Chem., Int. Ed. 2007, 46, 2768.
Kremzow et al. Chem. Eur. J. 2005 11:1833-1853.
Krimen, L. I. Org Synth 1970, 50, 1-3.
Martin, D.; Kehrli, S.; d'Augustin, M.; Clavier, H.; Mauduit, M.; Alexakis, A. J. Am. Chem. Soc. 2006, 128, 8416.
Roland, S.; Mangeney, P. Top. Organomet. Chem. 2005, 15, 191.
Tekavec, T. N.; Louie, J. Top. Organomet. Chem. 2007, 21, 159.

*Primary Examiner* — Michael Barker
(74) *Attorney, Agent, or Firm* — Bereskin & Parr LLP/S.E.N.C.R.L., s.r.l.; Michael Fenwick

(57) ABSTRACT

The current application relates to a metal catalyst of formula (I): $M[ADC][X]_n$, wherein M is a metal, ADC is a chiral acyclic diaminocarbene ligand, and X is a neutral or anionic ligand. The ADC ligand is prepared from the corresponding chiral formamidium salt precursor. The metal catalyst is used for asymmetric organic synthesis reactions such as hydrosilations, hydrogenations, conjugate additions, and cross-couplings.

12 Claims, 1 Drawing Sheet

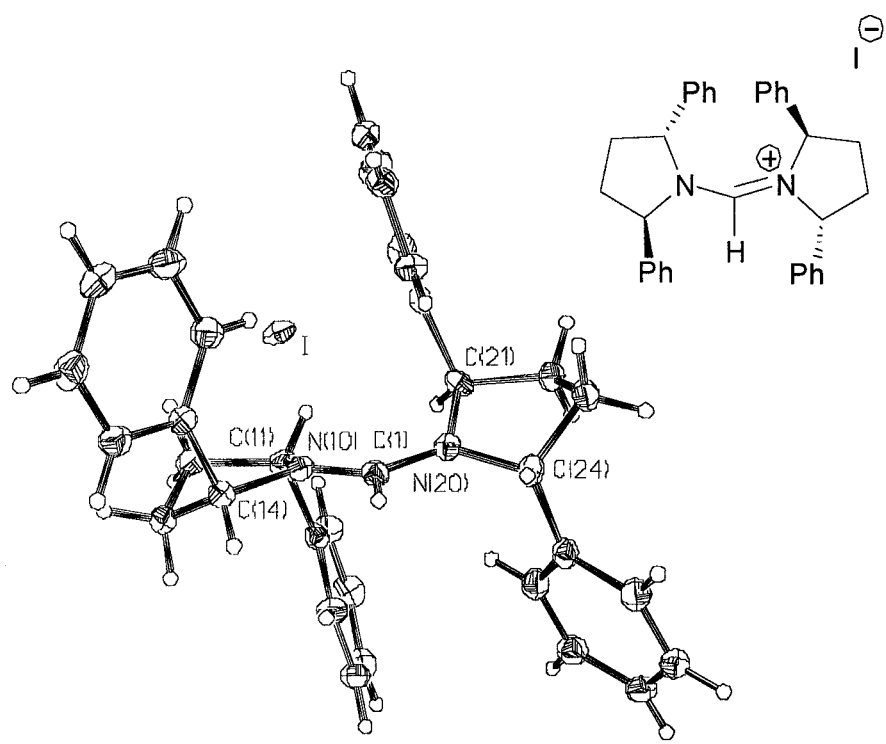

CHIRAL ACYCLIC DIAMINOCARBENE LIGANDS, PRECURSORS THEREFORE AND THEIR USE IN ORGANIC SYNTHESIS REACTIONS

This application is a national phase entry of PCT/CA2009/000928, filed Jul. 7, 2009, which claims priority from U.S. Provisional patent application Ser. No. 61/078,985 filed Jul. 8, 2008, each of these applications being incorporated herein in their entirety by reference.

FIELD OF THE DISCLOSURE

The present disclosure is in the field of metal catalysts for organic synthesis reactions, in particular to metal catalysts comprising a chiral acyclic diamino carbene ligand.

BACKGROUND OF THE DISCLOSURE

It is established that enantiomers can possess unique activities when interacting with chiral biological systems (e.g. enzymes).[1a] As a consequence, the pharmaceutical industry has migrated to manufacturing and marketing single enantiomeric forms of chiral drugs (e.g. 80% of small-molecule drugs approved by the FDA in 2006 were chiral and 75% were single enantiomers).[1a] The growing economic importance of single-enantiomer production has led to significant expansion of research into chiral synthesis.[1b]

The catalysis approach towards asymmetric synthesis offers several distinct advantages (e.g. cost savings, less waste generation) over more traditional protocols such as chiral stoichiometric reagents and chiral auxiliaries. In particular, transition metal (TM) catalysis has revolutionized organic synthesis.[2] The near constant improvement in the field of TM catalysis is undoubtedly due in large part to the introduction of new and improved ligands, which allows for desired transformations to be carried out in a more efficient manner (i.e. milder conditions, lower catalyst loadings, higher yields and higher enantioselectivities when applicable).

Recently, N-heterocyclic carbenes (NHC) have had a significant impact in the field of achiral TM catalysis. NHC (e.g. 1-3) have proven themselves to be viable, and in many cases, superior ligands to the more traditional phosphorus based ligands.[3]

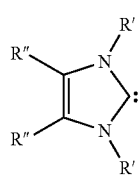

1

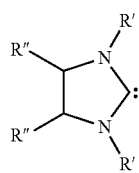

2

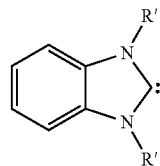

3

The improved characteristics of NHC flow from the fact that they are superior two electron donors to the TM centre.[4] Unfortunately, however, there are only a handful of TM-catalyzed transformations employing chiral NHC ligands that have afforded products with high enantioselectivities.[5] As a result, chiral phosphorus-based ligands continue to dominate the field of enantioselective catalysis.[1b]

Unlike NHC, acyclic diamino carbenes (ADC)[6] (4) have attracted scant attention from the synthetic community.[7]

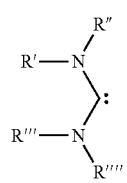

4

Certain achiral ADC have been examined in TM catalyzed cross-coupling reactions.[8] It was demonstrated that ADC are effective ligands for three important cross-couplings reactions viz Suzuki, Sonogashira and Heck reactions.[8]

SUMMARY OF THE DISCLOSURE

A new array of chiral ADC ligands that have been employed in enantioselective catalysis has been developed. A variety of symmetric and non-symmetric chiral acyclic formamidium salts have been prepared as precursors to their corresponding diamino carbenes. Various metal catalysts having these chiral ADC's as ligands have also been prepared and used in metal-catalyzed organic synthesis transformations.

Accordingly, the present disclosure includes a metal catalyst of the formula I:

$$M[ADC][X]_n \qquad (I)$$

wherein
M is a metal;
ADC is a chiral acyclic carbene of the formula II:

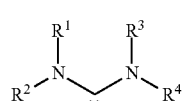

(II)

$R^1$, $R^2$, $R^3$ and $R^4$ are independently selected from $C_{1-10}$alkyl, $C_{2-10}$alkenyl, $C_{2-10}$alkynyl, $C_{3-10}$cycloalkyl, heteroaryl and aryl, each group being optionally substituted, or
$R^1$ and $R^2$ are linked to form, together with the nitrogen atom to which they are attached, an optionally substituted monocyclic or polycyclic, saturated or unsaturated ring system that contains 3 to 30 carbon atoms, of which one or more of the carbon atoms is optionally replaced with a heteromoiety selected from O, S, NH and $NC_{1-6}$alkyl, and/or $R^3$ and $R^4$ are linked to form, together with the nitrogen atom to which they are attached, an optionally substituted monocyclic or polycyclic, saturated or unsaturated ring system that contains 3 to 30 carbon atoms, of which one or more of the carbon atoms is optionally replaced with a heteromoiety selected from O, S, NH and $NC_{1-6}$alkyl, the optional substituents on $R^1$, $R^2$, $R^3$ and $R^4$ are independently selected from one or more of $C_{1-6}$alkyl, halo, halo-substituted $C_{1-6}$alkyl, $C_{3-10}$cycloalkyl, aryl and heteroaryl, and at least one of $R^1$, $R^2$, $R^3$, $R^4$, the ring system formed by $R^1$ and $R^2$ and the ring system formed by $R^3$ and $R^4$, or a substituent thereon, comprises at least one chiral center;

X is a neutral or an anionic ligand; and n is an integer representing the number of ligands, X, to fulfill the valency requirements of N, and when x is greater than 1, each X may be the same or different.

Accordingly, the present disclosure includes a chiral formamidium salt of the formula III:

(III)

wherein $R^1$, $R^2$, $R^3$ and $R^4$ are independently selected from $C_{1-10}$alkyl, $C_{2-10}$alkenyl, $C_{2-10}$alkynyl, $C_{3-10}$cycloalkyl, heteroaryl and aryl, each group being optionally substituted, or $R^1$ and $R^2$ are linked to form, together with the nitrogen atom to which they are attached, an optionally substituted monocyclic or polycyclic, saturated or unsaturated ring system that contains 3 to 30 carbon atoms, of which one or more of the carbon atoms is optionally replaced with a heteromoiety selected from O, S, NH and $NC_{1-6}$alkyl, and/or $R^3$ and $R^4$ are linked to form, together with the nitrogen atom to which they are attached, an optionally substituted monocyclic or polycyclic, saturated or unsaturated ring system that contains 3 to 30 carbon atoms, of which one or more of the carbon atoms is optionally replaced with a heteromoiety selected from O, S, NH and $NC_{1-6}$alkyl, the optional substituents on $R^1$, $R^2$, $R^3$ and $R^4$ are independently selected from one or more of $C_{1-6}$alkyl, halo, halo-substituted $C_{1-6}$alkyl, $C_{3-10}$cycloalkyl, aryl and heteroaryl, and at least one of $R^1$, $R^2$, $R^3$, $R^4$, the ring system formed by $R^1$ and $R^2$ and the ring system formed by $R^3$ and $R^4$, or a substituent thereon, comprises at least one chiral center; and Y is a non-coordinating counter anion.

The present disclosure also includes a method of performing metal-catalyzed organic synthesis reactions comprising contacting substrates for the organic synthesis reaction with a metal catalyst of the formula I as defined above under conditions for performing the organic synthesis reaction, and optionally isolating one or more products from the organic synthesis reaction. In an embodiment of the disclosure, the organic synthesis reaction is any reaction that benefits from the presence or use of a metal catalyst, for example, but not limited to, hydrosilations, hydrogenations, conjugate additions and cross-couplings. In an embodiment of the disclosure, the organic synthesis transformation is an asymmetric or chiral synthesis reaction (i.e. provides one enantiomer in excess of the other).

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The present disclosure will now be described in greater detail with reference to the attached drawings in which:

FIG. 1 is an X-ray crystal structure of (2R,5R)-1-(((2R,5R)-2,5-diphenylpyrrolidin-1-yl)methylene)-2,5-diphenylpyrrolidinium iodide (compound IIIj; Y=I⁻).

DETAILED DESCRIPTION OF THE DISCLOSURE (I) Definitions

The term "$C_{1-n}$alkyl" as used herein means straight and/or branched chain, saturated alkyl groups containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl group.

The term "$C_{1-n}$alkenyl" as used herein means straight and/or branched chain, unsaturated alkyl groups containing from one to n carbon atoms and one to three double bonds, and includes (depending on the identity of n) vinyl, allyl, 2-methylprop-1-enyl, but-1-enyl, but-2-enyl, but-3-enyl, 2-methylbut-1-enyl, 2-methyl-pent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl group.

The term "$C_{1-n}$alkynyl" as used herein means straight and/or branched chain, unsaturated alkyl groups containing from one to n carbon atoms and one to three bonds, and includes (depending on the identity of n) propargyl, 2-methylprop-1-ynyl, but-1-ynyl, but-2-ynyl, but-3-ynyl, 2-methylbut-1-ynyl, 2-methylpent-1-ynyl, 4-methylpent-1-ynyl, 4-methylpent-2-ynyl, 2-methylpent-2-ynyl, 4-methylpenta-1,3-diynyl, hexyn-1-yl and the like, where the variable n is an integer representing the largest number of carbon atoms in the alkynyl group.

The term "$C_{3-n}$cycloalkyl" as used herein means a monocyclic, bicyclic or tricyclic saturated carbocylic group containing from three to n carbon atoms and includes (depending on the identity of n) cyclopropyl, cyclobutyl, cyclopentyl, cyclodecyl and the like, where the variable n is an integer representing the largest number of carbon atoms in the cycloalkyl group.

The term "aryl" as used herein means a monocyclic, bicyclic or tricyclic aromatic ring system containing from 6 to 14 carbon atoms and at least one aromatic ring and includes phenyl, naphthyl, anthracenyl, 1,2-dihydronaphthyl, 1,2,3,4-tetrahydronaphthyl, fluorenyl, indanyl, indenyl and the like.

The term "heteroaryl" as used herein means a monocyclic, bicyclic or tricyclic ring system containing one or two aromatic rings and from 5 to 14 atoms of which, unless otherwise specified, one, two, three, four or five are heteroatoms independently selected from N, NH, N($C_{1-6}$alkyl), O and S and includes thienyl, furyl, pyrrolyl, pyrididyl, indolyl, quinolyl, isoquinolyl, tetrahydroquinolyl, benzofuryl, benzothienyl and the like.

The term "halo" as used herein means halogen and includes chloro, fluoro, bromo and iodo.

The term "ring system" as used herein refers to a carbon-containing ring system, that includes monocycles, fused bicyclic and polycyclic rings and bridged rings. Where specified, the carbons in the rings may be substituted or replaced with heteroatoms.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Catalysts and Ligands

The present disclosure includes a metal catalyst of the formula I:

M[ADC][X]$_n$  (I)

wherein
M is a metal;
ADC is a chiral acyclic carbene of the formula II:

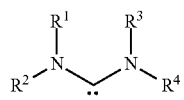

(II)

$R^1$, $R^2$, $R^3$ and $R^4$ are independently selected from $C_{1-10}$alkyl, $C_{2-10}$alkenyl, $C_{2-10}$alkynyl, $C_{3-10}$cycloalkyl, heteroaryl and aryl, each group being optionally substituted, or
$R^1$ and $R^2$ are linked to form, together with the nitrogen atom to which they are attached, an optionally substituted monocyclic or polycyclic, saturated or unsaturated ring system that contains 3 to 30 carbon atoms, of which one or more of the carbon atoms is optionally replaced with a heteromoiety selected from O, S, NH and N$C_{1-6}$alkyl, and/or
$R^3$ and $R^4$ are linked to form, together with the nitrogen atom to which they are attached, an optionally substituted monocyclic or polycyclic, saturated or unsaturated ring system that contains 3 to 30 carbon atoms, of which one or more of the carbon atoms is optionally replaced with a heteromoiety selected from O, S, NH and N$C_{1-6}$alkyl,
the optional substituents on $R^1$, $R^2$, $R^3$ and $R^4$ are independently selected from one or more, optionally one to five, suitably one to three, of $C_{1-6}$alkyl, halo, halo-substituted $C_{1-6}$alkyl, $C_{3-10}$cycloalkyl, aryl and heteroaryl, and at least one of $R^1$, $R^2$, $R^3$, $R^4$, the ring system formed by $R^1$ and $R^2$ and the ring system formed by $R^3$ and $R^4$, or a substituent thereon, comprises at least one chiral center;

X is a neutral or an anionic ligand; and n is an integer representing the number of ligands, X, to fulfill the valency requirements of N, and when x is greater than 1, each X may be the same or different.

In an embodiment of the disclosure $R^1$, $R^2$, $R^3$ and $R^4$ in the ADC's of formula II are independently selected from $C_{1-6}$alkyl, $C_{5-6}$cycloalkyl and aryl, each group being optionally substituted, or $R^1$ and $R^2$ and/or $R^3$ and $R^4$ are linked to form, together with the nitrogen atom to which they are attached, an optionally substituted monocyclic, saturated ring system that contains 4 to 7 carbon atoms, and the optional substituents on $R^1$, $R^2$, $R^3$ and $R^4$ are independently selected from one or more, optionally one to five, suitably one to three, of $C_{1-4}$alkyl, halo-substituted $C_{1-4}$alkyl, $C_{5-6}$cycloalkyl and aryl, and at least one of $R^1$, $R^2$, $R^3$, $R^4$, the ring system formed by $R^1$ and $R^2$ and the ring system formed by $R^3$ and $R^4$, or a substituent thereon, comprises at least one chiral center.

In a further embodiment of the disclosure, ADC of formula II is selected from:

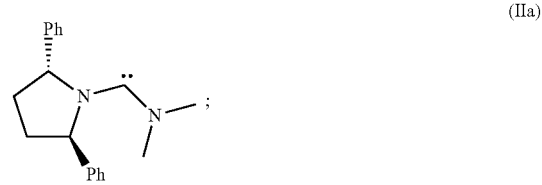

(IIa)

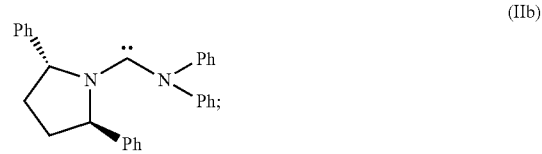

(IIb)

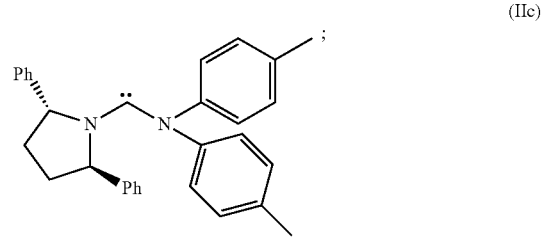

(IIc)

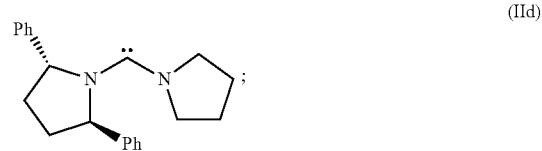

(IId)

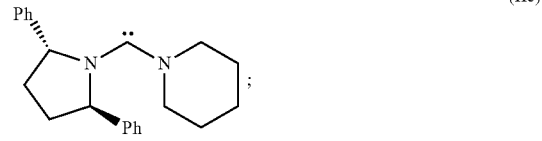

(IIe)

(IIIf)

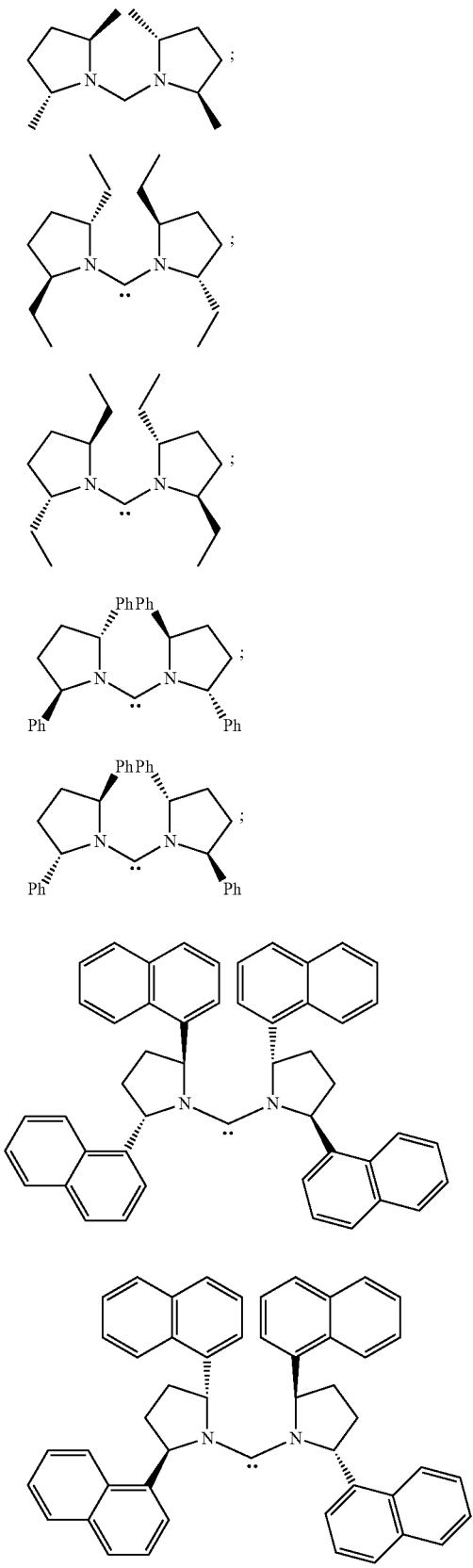

and analogs of the above compounds that are substituted on the alkyl groups, phenyl rings, aromatic and/or pyrrolidine rings with one or more substituents independently selected from $C_{1-6}$alkyl, halo, halo-substituted $C_{1-6}$alkyl, $OC_{1-6}$alkyl and halo-substituted $OC_{1-6}$alkyl.

The metal M may be any metal used in catalysts for metal-catalyzed organic synthesis reactions. In an embodiment of the invention, the metal is any transition metal, or other metal selected from B, Al, Ga, Ge, In, Sn, Sb, Ti, Pb, Bi and Po, or a lanthanide or actinide. Examples of suitable metals include, but are not limited to Cu, Ag, Au, Sn, Ni, Pd, Pt, Co, Rh, Ir, Fe, Ru, Os and Re.

In an embodiment of the disclosure, X is selected from any ancillary ligand, including phosphine, amine, alkene, diamine, diphosphine, aminophosphine, halo (for example, fluoro, chloro, bromo or iodo, specifically chloro), HO⁻, $R^5O^-$ and $R^5C(O)O^-$, wherein $R^5$ is H or $C_{1-6}$alkyl. In an embodiment of the disclosure, X is chloro. When n is greater than 1, it is an embodiment of the disclosure that all X ligands are the same. X may also be a multidentate ligand.

A person skilled in the art would appreciate that n is an integer that will depend on the identity and oxidation state of M and the identity of X.

The preparation of the catalysts of formula I is suitably done by generating the ADC ligand in situ from a formamidium salt of formula III, followed by addition of an appropriate metal precursor complex or salt:

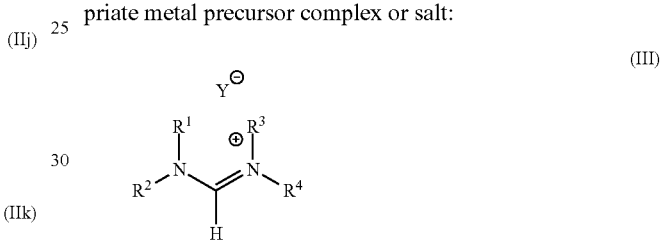

wherein
$R^1$, $R^2$, $R^3$ and $R^4$ are as defined in formula II and Y is a non-coordinating counter anion. Suitably the ADC of formula II is generated from a formamidium salt of formula III by reaction with a strong base, such as an alkyl lithium or lithium amide, at reduced temperatures, for example at −50° C. to about −90° C. The resulting reaction mixture is then reacted for a time and at a temperature sufficient for the formation of the ADC of formula II (determinable by a person skilled in the art), then the appropriate metal compound is added, suitably at reduced temperatures, for example at −50° C. to about −90° C., to form the catalysts of formula I. A person skilled in the art would appreciate that the reaction times and temperatures can be varied, depending on the identity of the compounds of formula II and metal precursor compound, to optimize the yield of the catalysts of formula I. The catalysts of formula I, so prepared, may be used without isolation in any organic synthesis transformation.

The present disclosure further includes a formamidium salt useful as a precursor to the chiral ADC's of the present disclosure. Accordingly, the present disclosure includes a chiral formamidium salt of the formula III:

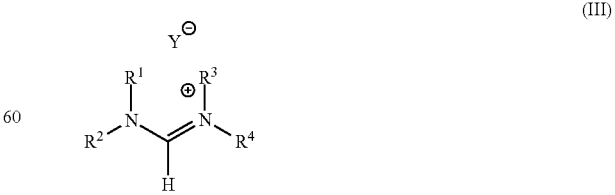

wherein
$R^1$, $R^2$, $R^3$ and $R^4$ are independently selected from $C_{1-10}$alkyl, $C_{2-10}$alkenyl, $C_{2-10}$alkynyl, $C_{3-10}$cycloalkyl, heteroaryl and aryl, each group being optionally substituted, or $R^1$ and $R^2$ are linked to form, together with the nitrogen atom to which they are attached, an optionally substituted monocyclic or polycyclic, saturated or unsaturated ring system that contains 3 to 30 carbon atoms, of which one or more of the carbon atoms is optionally replaced with a heteromoiety selected from O, S, NH and $NC_{1-6}$alkyl, and/or
$R^3$ and $R^4$ are linked to form, together with the nitrogen atom to which they are attached, an optionally substituted monocyclic or polycyclic, saturated or unsaturated ring system that contains 3 to 30 carbon atoms, of which one or more of the carbon atoms is optionally replaced with a heteromoiety selected from O, S, NH and $NC_{1-6}$alkyl,
the optional substituents on $R^1$, $R^2$, $R^3$ and $R^4$ are independently selected from one or more, optionally one to five, suitably one to three, of $C_{1-6}$alkyl, halo, halo-substituted $C_{1-6}$alkyl, $C_{3-10}$cycloalkyl, aryl and heteroaryl, and
at least one of $R^1$, $R^2$, $R^3$, $R^4$, the ring system formed by $R^1$ and $R^2$ and the ring system formed by $R^3$ and $R^4$, or a substituent thereon, comprises at least one chiral center; and
Y is a non-coordinating counter anion.

In an embodiment of the disclosure $R^1$, $R^2$, $R^3$ and $R^4$ in the formamidium salts of formula III are independently selected from $C_{1-6}$alkyl, $C_{5-6}$cycloalkyl and aryl, each group being optionally substituted, or $R^1$ and $R^2$ and/or $R^3$ and $R^4$ are linked to form, together with the nitrogen atom to which they are attached, an optionally substituted monocyclic, saturated ring system that contains 4 to 7 carbon atoms, and the optional substituents on $R^1$, $R^2$, $R^3$ and $R^4$ are independently selected from one or more, optionally one to five, suitably one to three, of $C_{1-4}$alkyl, halo-substituted $C_{1-4}$alkyl, $C_{5-6}$cycloalkyl and aryl, and at least one of $R^1$, $R^2$, $R^3$, $R^4$, the ring system formed by $R^1$ and $R^2$ and the ring system formed by $R^3$ and $R^4$, or a substituent thereon, comprises at least one chiral center.

In a further embodiment of the disclosure, Y is any non-coordinating counter anion, including, for example, $BF_4^-$ or $B(C_6F_5)_4^-$.

In an embodiment of the disclosure, the formamidium salt of formula (III) is selected from:

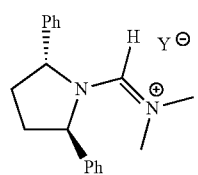
(IIIa)

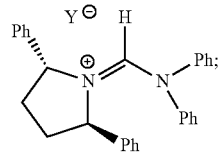
(IIIb)

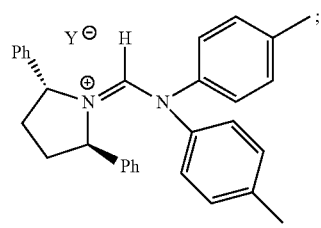
(IIIc)

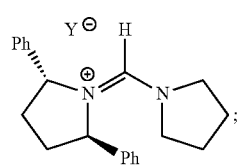
(IIId)

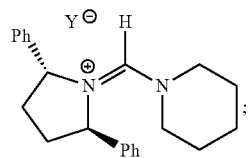
(IIIe)

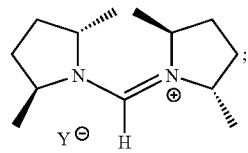
(IIIf)

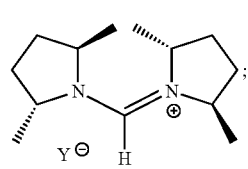
(IIIg)

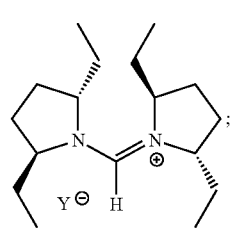
(IIIh)

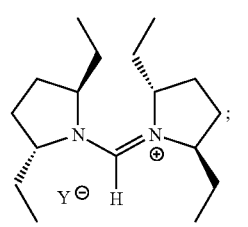
(IIIi)

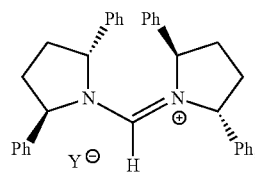
(IIIj)

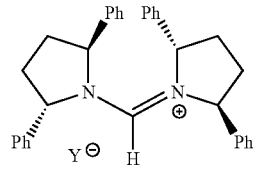
(IIIk)

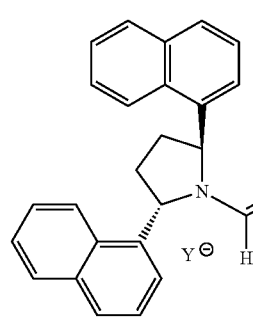
(IIIl)

and

-continued

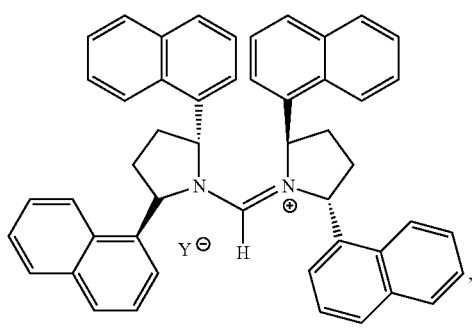

(IIIm)

where Y is a counteranion, and analogs of the above compounds that are substituted on the alkyl groups, phenyl rings, aromatic and/or pyrrolidine rings with one or more substituents independently selected from $C_{1-6}$alkyl, halo, halo-substituted $C_{1-6}$alkyl, $OC_{1-6}$alkyl and halo-substituted $OC_{1-6}$alkyl.

The formamidium salts of formula III may be prepared, for example, by reacting an aldehyde of formula IV with an amine of the formula V under Vilsmeier Haack reaction conditions, for example in the presence of $POCl_3$, or equivalent reagent, at reduced temperatures (e.g. about 10° C. to −90° C.) in an inert anhydrous solvent.

wherein $R^1$, $R^2$, $R^3$ and $R^4$ are as defined in formula III. Suitably the $POCl_3$, or equivalent reagent, is added to the compound of formula IV at about −50° C. to about −90° C., followed by warming to room temperature for a time sufficient to form the intermediate iminium salt and the resulting mixture is cooled to about 5° C. to about −5° C. and the amine of formula V is added. A person skilled in the art would appreciate that the reaction times and temperatures can be varied, depending on the identity of the compounds of formula IV and V, to optimize the yield of the compounds of formula III. The compounds of formula IV and V are either commercially available or may be prepared using methods known in the art, for example as described herein below.

(III) Methods of the Disclosure

The present disclosure also includes a method of performing metal-catalyzed organic synthesis reactions comprising contacting substrates for the organic synthesis reaction with a metal catalyst of the formula I as defined above under conditions for performing the organic synthesis reaction, and optionally isolating one or more products from the organic synthesis reaction. In an embodiment of the disclosure, the organic synthesis reaction is any reaction the benefits from the presence or use of a metal catalyst, for example, but not limited to, hydrosilations, hydrogenations, conjugate additions and cross-couplings (for example Suzuki, Sonogashira and Heck reactions). In an embodiment of the disclosure, the organic synthesis transformation is an asymmetric or chiral synthesis reaction (i.e. provides one enantiomer in excess of the other).

In an embodiment of the disclosure, the catalyst of formula I is generated in situ in solution and the resulting catalyst solution is added to the appropriate starting materials for the organic synthesis transformation.

The following non-limiting examples are illustrative of the present disclosure:

(IV) Examples

Materials and Methods

All reactions were carried out under nitrogen atmosphere; solvents were dried using standard techniques. All secondary amines and secondary formamides were obtained from Sigma Aldrich and were used as received except R,R-2,5-diphenylpyrrolidine and R,R—N-formyl-2,5-diphenylpyrrolidine which were synthesized according to the reported procedures.[9-11]

Example 1

General Procedure to Synthesize Formamidinium Salts

The formamidinium salts were synthesized through Vilsmeier-Haack chemistry according to a modified procedure reported by Alder et al.[12] To a solution of an appropriate secondary formamide in dry dichloromethane was added one equivalent of $POCl_3$ at −78° C. and the mixture was allowed to warm to room temperature and stirred for two hours. The mixture was cooled to 0° C. and a solution of one equivalent of an appropriate secondary amine and one equivalent of triethylamine in dichloromethane was added, it was again allowed to warm to room temperature and stirred for two hours. The solvent was removed in vacuo, the crude product was dissolved in $CH_2Cl_2$ and washed extensively with saturated aqueous $NaBF_4$. The organic layer was separated, dried ($MgSO_4$), filtered and evaporated in vacuo. The crude product was the purified by column chromatography [silica gel, MeOH/$CH_2Cl_2$ (1:10)].

(a) (R,R,R,R)-2,5-diphenylpyrrolidin-1-ylmethylene (2,5-diphenylpyrrolidinium) tetrafluoroborate (compound IIIj) & (S,S,S,S)-2,5-diphenylpyrrolidin-1-ylmethylene(2,5-diphenylpyrrolidinium) tetrafluoroborate (compound IIIk)

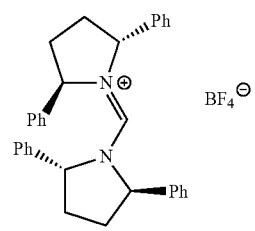

IIIj

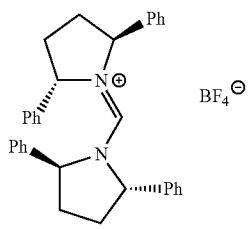

IIIk

These compounds were prepared from (R,R)—N-formyl-2,5-diphenylpyrrolidine or (S,S)—N-formyl-2,5-diphenylpyrrolidine and (R,R)-2,5-diphenylpyrrolidine or (S,S)-2,5-diphenylpyrrolidine to give a low melting yellow solid in 78-80% yield. $^1$H NMR [CDCl$_3$, 500 MHz] δ: 9.67 (s, 1H), 7.44-7.37 (m, 6H), 7.20-7.13 (m, 10H) 6.78-6.76 (m, 4H), 5.92-5.90 (m, 2H), 4.95-4.93 (m, 2H), 2.34-2.20 (m, 4H), 1.68-1.60 (m, 2H); $^{13}$C NMR [CDCl$_3$, 75 MHz] δ: 155.81, 140.95, 140.88, 130.17, 129.08, 128.96, 128.30, 126.33, 124.89, 70.88, 64.63, 33.59, 29.65.

(b) (R,R,R,R)-2,5-dimethylpyrrolidin-1-ylmethylene (2,5-dimethylpyrrolidinium) tetrafluoroborate (compound IIIf) & (S,S,S,S)-2,5-dimethylpyrrolidin-1-ylmethylene(2,5-dimethylpyrrolidinium) tetrafluoroborate (compound IIIg)

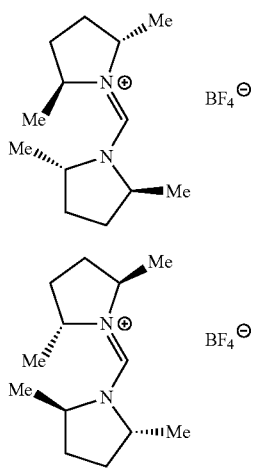

IIIf

IIIg

These compounds were prepared from (R,R)—N-formyl-2,5-dimethylpyrrolidine or (S,S)—N-formyl-2,5-dimethylpyrrolidine and (R,R)-2,5-dimethylpyrrolidine or (R,R)-2,5-dimethylpyrrolidine to give a low melting yellow solid in 60-65% yield. $^1$H NMR [CDCl$_3$, 500 MHz] δ: 8.10 (s, 1H), 4.40-4.20 (m, 4H), 2.20-1.80 (m, 6H), 1.80-1.60 (m, 2H), 1.55 (6H, d, J=7.5 Hz), 1.50 (6H, d, J=7.5 Hz).

(c) (R,R,R,R)-2,5-diethylpyrrolidin-1-ylmethylene(2,5-diethylpyrrolidinium) tetrafluoroborate (compound IIIh) & (S,S,S,S)-2,5-diethylpyrrolidin-1-ylmethylene(2,5-diethylpyrrolidinium) tetrafluoroborate (compound IIIi)

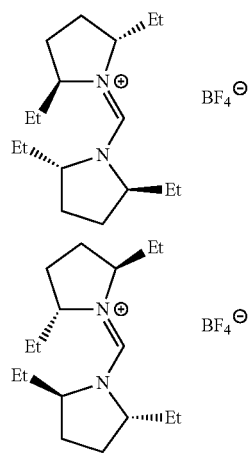

IIIh

IIIi

These compounds were prepared from (R,R)—N-formyl-2,5-diethylpyrrolidine or (S,S)—N-formyl-2,5-diethylpyrrolidine and (R,R)-2,5-diethylpyrrolidine or (R,R)-2,5-diethylpyrrolidine to give a low melting yellow solid in 60-65% yield. $^1$H NMR [CDCl$_3$, 500 MHz] δ: 7.95 (s, 1H), 4.40-4.20 (m, 4H), 2.21-1.70 (m, 8H), 1.68 (4H, q, J=7.5 Hz), 1.63 (4H, t, J=7.5 Hz), 1.35 (6H, d, J=7.5 Hz), 1.30 (6H, d, J=7.5 Hz).

(c) (2S,5S)-1-(((2S,5S)-2,5-di(naphthalen-1-yl)pyrrolidin-1-yl)methylene)-2,5-di(naphthalen-1-yl)pyrrolidinium tetrafluoroborate (compound IIIl) & (2R,5R)-1-(((2R,5R)-2,5-di(naphthalen-1-yl)pyrrolidin-1-yl)methylene)-2,5-di(naphthalen-1-yl) pyrrolidinium tetrafluoroborate (compound IIIm)

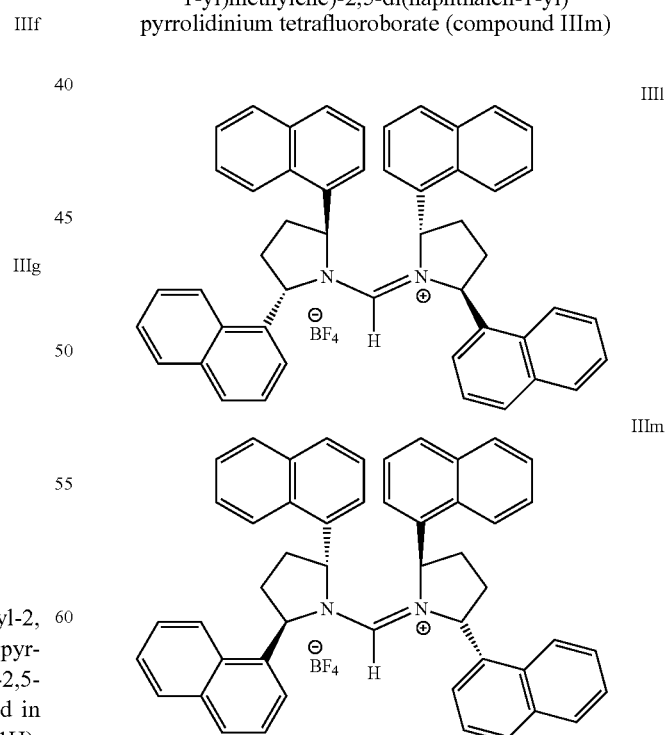

IIIl

IIIm

These compounds were prepared from (2S,5S)-2,5-di(naphthalen-1-yl)pyrrolidine-1-carbaldehyde or (2R,5R)-2,5-di (naphthalen-1-yl)pyrrolidine-1-carbaldehyde and (2S,5S)-2,5-di(naphthalen-1-yl)pyrrolidine or (2R,5R)-2,5-di(naphthalen-1-yl)pyrrolidine to give a yellow-brown solid in 40-50% yield.

(b) (R,R)-2,5-diphenylpyrrolidin-1-ylmethylene-(N,N-dimethylammonium) tetrafluoroborate (compound IIIa)

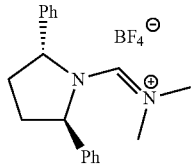 [SMILES: C[N+](C)=CN1[C@@H](c2ccccc2)CC[C@@H]1c1ccccc1 ; "BF4"]

This compound was prepared from N,N-dimethyl formamide and (R,R)-2,5-diphenylpyrrolidine to give a low melting point clear yellow solid in 95% yield. $^1$H NMR [CDCl$_3$, 300 MHz] δ: 8.43 (s, 1H), 7.39-7.19 (m, 10H), 5.99-5.97 (m, 2H), 3.12 (s, 3H), 2.93 (s, 3), 2.71-2.69 (m, 1H), 2.34-3.32 (m, 1H), 1.89-1.86 (m, 2H). $^{13}$C NMR [CDCl$_3$, 75 MHz] δ: 156.32, 141.28, 140.75, 129.66, 129.21, 128.30, 126.77, 125.10, 69.89, 64.54, 46.36, 39.02, 34.82, 30.10.

(c) (R,R)—(N,N-diphenylamino)-N-ylmethylene(2,5-diphenylpyrrolidinium) tetrafluoroborate (compound IIIb)

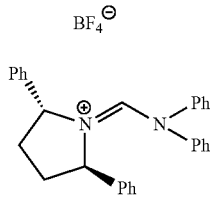 [SMILES: "BF4" ; C(N(c1ccccc1)c1ccccc1)=[N+]1[C@@H](c2ccccc2)CC[C@@H]1c1ccccc1]

This compound was prepared from (R,R)—N-formyl-2,5-diphenylpyrrolidine and diphenyl amine, and a low melting point dark brown solid was obtained in 96% yield. $^1$H NMR [CDCl$_3$, 500 MHz] δ: 9.08 (s, 1H), 7.60-7.55 (m, 5H), 7.44-7.39 (m, 3H), 7.33-7.31 (m, 4H), 7.26-7.23 (m, 4H), 7.17-7.16 (m, 3H), 6.95-6.93 (m, 1H), 5.92-5.90 (d, 1H), 4.62-4.59 (m, 1H), 2.62-2.54 (m, 2H), 2.06-1.96 (m, 2H). $^{13}$C NMR [CDCl$_3$, 75 MHz] δ: 153.14, 143.23, 140.78, 138.52, 137.87, 129.97, 129.86, 129.72, 129.46, 129.38, 129.11, 128.94, 128.79, 128.04, 127.52, 126.57, 125.15, 124.45, 71.57, 67.42, 36.08, 32.01.

(d) (R,R)—(N,N-di-p-tolylamino)-N-ylmethylene(2,5-diphenylpyrrolidinium) tetrafluoroborate (compound IIIc)

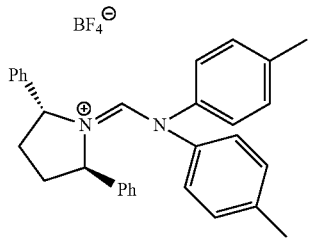 [SMILES: Cc1ccc(N(C=[N+]2[C@@H](c3ccccc3)CC[C@@H]2c2ccccc2)c2ccc(C)cc2)cc1 ; "BF4"]

This compound was prepared from (R,R)—N-formyl-2,5-diphenylpyrrolidine and di-p-tolyl amine, and a low melting point dark red solid was obtained in 97% yield. $^1$H NMR [CDCl$_3$, 300 MHz] d: 8.13 (s, 1H), 7.63-7.53 (m, 2H), 7.53-7.42 (m, 3H), 7.36-7.28 (m, 3H), 7.22-7.16 (m, 3H), 7.03-6.93 (m, 5H), 6.68-6.66 (m, 1H), 6.08-6.04 (m, 1H), 5.78-5.75 (m, 1H), 4.92-4.87 (m, 1H), 2.70-2.63 (m, 1H), 2.54-2.47 (m, 1H), 2.39 (s, 3H), 2.19 (s, 3H), 1.97-1.90 (m, 1H). $^{13}$C NMR [CDCl$_3$, 75 MHz] d: 152.30, 141.05, 140.61, 139.80, 139.15, 138.60, 135.40, 130.48, 129.80, 129.71, 129.06, 127.99, 127.63, 127.11, 126.38, 125.01, 124.07, 121.71, 71.85, 67.30, 36.14, 32.28, 21.30, 20.92.

(e) (R,R)-2,5-diphenylpyrrolidin-1-ylmethylenepyrrolidinium tetrafluoroborate (compound IIId)

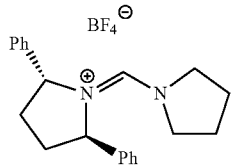 [SMILES: C(N1CCCC1)=[N+]1[C@@H](c2ccccc2)CC[C@@H]1c1ccccc1 ; "BF4"]

This compound was prepared from N-formyl pyrrolidine and (R,R)-2,5-diphenylpyrrolidine to form a clear yellow low melting point solid in 82% yield. $^1$H NMR [CDCl$_3$, 500 MHz] δ: 9.00 (s, 1H), 7.46-7.31 (m, 10H), 6.04-6.03 (d, 1H), 5.82-5.80 (d, 1H), 4.03-4.01 (m, 1H), 3.85-3.83 (m, 1H), 3.63-3.61 (m, 1H), 3.05-3.03 (m, 1H), 2.76-2.74 (m, 1H), 2.44-2.42 (m, 1H), 1.98-1.65 (m, 6H). $^{13}$C NMR [CDCl$_3$, 75 MHz] δ: 152.94, 141.25, 140.93, 129.82, 129.49, 128.63, 128.34, 127.00, 124.89, 69.52, 64.26, 55.40, 48.42, 34.41, 30.44, 25.87, 23.69.

(f) (R,R)-2,5-diphenylpyrrolidin-1-ylmethylenepiperidinium tetrafluoroborate (compound IIIe)

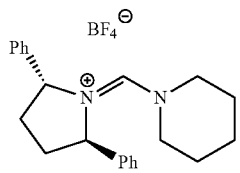 [SMILES: C(N1CCCCC1)=[N+]1[C@@H](c2ccccc2)CC[C@@H]1c1ccccc1 ; "BF4"]

This compound was prepared from N-formyl piperidine and (R,R)-2,5-diphenylpyrrolidine to form a clear yellow low melting point solid in 93% yield. $^1$H NMR [CDCl$_3$, 300 MHz] δ 8.97 (s, 1H), 7.47-7.27 (m, 10H), 6.22-6.20 (d, 1H), 5.59-5.56 (d, 1H), 3.78-3.74 (m, 1H), 3.54-3.42 (m, 2H), 3.33-3.29 (m, 1H), 2.57-2.54 (m, 1H), 2.30-2.28 (m, 1H), 2.02-1.99 (m, 2H), 1.65-1.61 (m, 2H), 1.42-1.40 (m, 2H), 1.24-1.19 (m, 1H), 0.54-0.50 (m, 1H). $^{13}$C NMR [CDCl$_3$, 75 MHz] δ: 153.61, 141.31, 139.41, 129.61, 129.16, 128.35, 128.23, 126.66, 125.65, 70.29, 64.85, 56.04, 48.64, 35.15, 30.20, 26.09, 24.73, 22.84.

Example 2

General Procedure for the Hydrosilylation of Ketones (a) Synthesis of Chiral Rhodium Catalyst

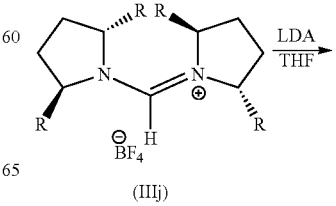

-continued

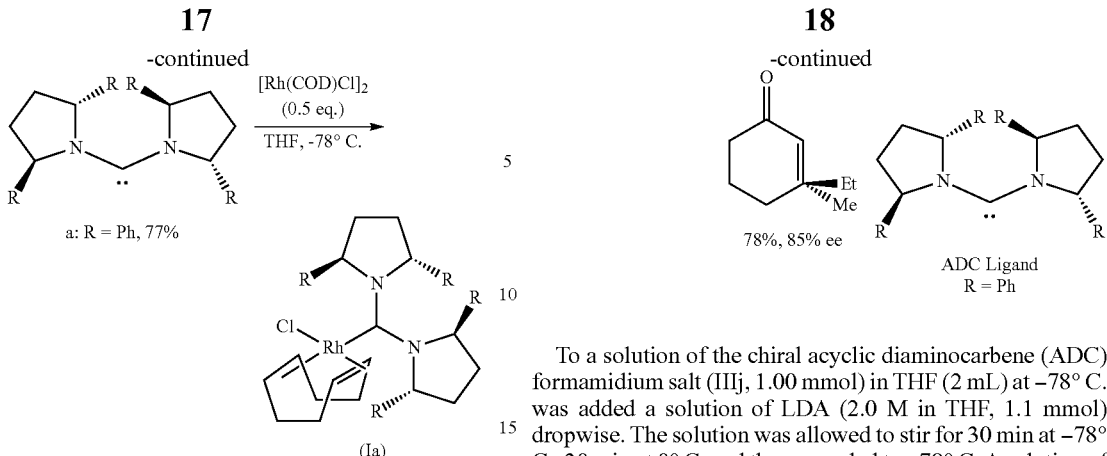

a: R = Ph, 77%

To a solution of the chiral acyclic diaminocarbene (ADC) formamidium salt (IIIj, 1.00 mmol) in THF (2 mL) at −78° C. was added a solution of LDA (2.0 M in THF, 1.1 mmol) dropwise. The solution was allowed to stir for 30 min at −78° C., 30 min at 0° C. and then recooled to −78° C. A solution of [Rh(COD)Cl]$_2$ (0.45 mmol) in THF (1 mL) was then added dropwise, and the reaction mixture was allowed to stir for 1 h while warming to rt. The chiral rhodium ADC complex (Ia) was generated in situ.

(b) Enantioselective Hydrosilylation of Ketones Using a Chiral Rhodium ADC Catalyst

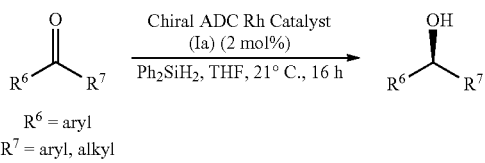

$R^6$ = aryl
$R^7$ = aryl, alkyl a) $R^6$ = Ph, $R^7$ = Me, 83%, 97% ee
b) $R^6$ = Ph, $R^7$ = $^i$Pr, 69%, 93% ee
c) $R^6$ = C$_6$H$_{11}$, $R^7$ = Me, 77%, 90% ee In another flask was added the aryl ketone (1.00 mmol) and PhSiH$_2$ (1.50 mmol) and THF (4 mL). A solution of the Rh-carbene complex prepared in Example 2(a) (0.25 M in THF, 0.02 mmol) was the added. The reaction mixture was stirred for 24 h at rt. The reaction mixture was then quenched with the addition of water (1.5 mL) and 0.5N HCl (0.5 mL). The resulting mixture was stirred for another hour at rt. The organic components were then extracted with Et$_2$O (5×10 mL). The organic extracts were then dried (MgSO$_4$), filtered and concentrated in vacuo to afford a clear, colourless oil. The residue was purified by column chromatography (silica gel, EtOAc/hexanes) to provide the chiral secondary alcohols. The enantioselectivities were assayed by chiral HPLC. The yields and ee's are shown above.

Example 3

Enantioselective Conjugate Addition Using a Chiral Copper ADC Catalyst

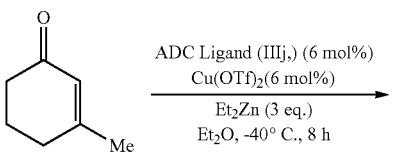

To a solution of the chiral acyclic diaminocarbene (ADC) formamidium salt (IIIj, 1.00 mmol) in THF (2 mL) at −78° C. was added a solution of LDA (2.0 M in THF, 1.1 mmol) dropwise. The solution was allowed to stir for 30 min at −78° C., 30 min at 0° C. and then recooled to −78° C. A solution of Cu(OTf)$_2$ (1.00 mmol) in THF (1 mL) was then added dropwise, and the reaction mixture was allowed to stir for 1 h while warming to rt. The presumed chiral copper ADC complex was thus generated in situ.

In another flask was added the enone (1.00 mmol) and Et$_2$O (3.00 mL). The mixture was cooled to −40° C. The chiral copper-ADC complex prepared above was then added (0.25 M, 0.06 mmol). The mixture was stirred for 15 min and then Et$_2$Zn was added (3 mmol). The resulting reaction mixture was stirred for 8 h at −40° C. The reaction mixture was then quenched with the addition of water (1.5 mL) and 0.5N HCl (0.5 mL). The resulting mixture was stirred for another hour at rt. The organic components were then extracted with Et$_2$O (5×10 mL). The organic extracts were then dried (MgSO$_4$), filtered and concentrated in vacuo to afford a yellow oil. The residue was purified by column chromatography (silica gel, EtOAc/hexanes) to provide the chiral secondary alcohols. The enantioselectivity was assayed by chiral HPLC. The yields and ee's are shown in the equation above.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATION FOR DOCUMENTS REFERRED TO IN THE SPECIFICATION 1. (a) Thayer, A. *M Chem. Eng. News* 2007, 85, Issue 32, 11.
   (b) *Comprehensive Asymmetric Catalysis*, Jacosen, E. N., Pfaltz, A., Yamamoto, H., Eds.; Springer-Verlag: Berlin, Vol. 1-3, 1999.
2. Tsuji, J. *Transition Metal Reagens and Catalysts*; Wiley: West Sussex, England, 2002.
3. For recent reviews, see: (a) Kantchev, E. A. B.; O'Brien, C. J.; Organ, M. G. *Angew Chem., Int. Ed.* 2007, 46, 2768. (b) Tekavec, T. N.; Louie, J. *Top. Organomet. Chem.* 2007, 21, 159.
4. Cavallo, L.; Correa A.; Costabile, C; Jacobsen, H. *J. Organomet. Chem.* 2005, 690, 5407.
5. (a) Gillingham D. G.; Hoveyda, A. H. *Angew. Chem., Int. Ed.* 2007, 46, 3860. (b) Martin, D.; Kehrli, S.; d'Augustin, M.; Clavier, H.; Mauduit, M.; Alexakis, A. *J. Am. Chem. Soc.* 2006, 128, 8416. (c) For a recent review, see: Roland, S.; Mangeney, P. *Top. Organomet. Chem.* 2005, 15, 191.

6. For the first isolation of an ADC, see: Alder, R. W.; Allen, P. R.; Murray, M.; Orpen, A. G. *Angew. Chem., Int. Ed.* 1996, 35, 1121.
7. For recent reports on ADC, see: (a) Frey, G. D.; Herdtweck, E.; Herrmann, W. A. *J. Organomet. Chem.* 2006, 691, 2465. (b) Herrmann, W. A.; Schütz.; Frey, G. D.; Herdtweck, E. *Organometallics* 2006, 25, 2437. (c) Kremzow, D.; Seidel, G.; Lehmann, C. W.; Fürstner, A. *Chem. Eur. J.* 2005, 11, 1833.
8. Dhudshia, B.; Thadani, A. N. *Chem. Commun.* 2006, 668.
9. Michael Chong, J.; Clarke, I. S.; Koch, I.; Olbach, P. C.; Taylor, N. J. *Tetrahedron: Asymmetry* 1995, 6, 409-418.
10. Iseki, K.; Mizuno, S.; Kuroki, Y.; Kobayashi, Y. *Tetrahedron* 1999, 55, 977-988.
11. Krimen, L. I. *Org Synth* 1970, 50, 1-3.
12. Alder, R. W.; Blake, M. E.; Bufali, S.; Butts, C. P.; Orpen, A. G.; Schutz, J.; Williams, S. J. *J. Chem. Soc., Perkin Trans.* 12001, 1586-1593.

We claim:

1. A metal catalyst of the formula I:

$$M[ADC][X]_n \quad (I)$$

wherein
M is a metal;
ADC is a chiral acyclic carbene of the formula II:

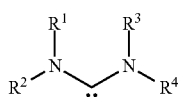

(II)

$R^1$, $R^2$, $R^3$ and $R^4$ are independently selected from $C_{1-10}$alkyl, $C_{2-10}$alkenyl, $C_{2-10}$alkynyl, $C_{3-10}$cycloalkyl, heteroaryl and aryl, each group being optionally substituted, or $R^1$ and $R^2$ are linked to form, together with the nitrogen atom to which they are attached, an optionally substituted monocyclic or polycyclic, saturated or unsaturated ring system that contains 3 to 30 carbon atoms, of which one or more of the carbon atoms is optionally replaced with a heteromoiety selected from O, S, NH and $NC_{1-6}$alkyl, and/or $R^3$ and $R^4$ are linked to form, together with the nitrogen atom to which they are attached, an optionally substituted monocyclic or polycyclic, saturated or unsaturated ring system that contains 3 to 30 carbon atoms, of which one or more of the carbon atoms is optionally replaced with a heteromoiety selected from O, S, NH and $NC_{1-6}$alkyl, the optional substituents $R^1$, $R^2$, $R^3$ and $R^4$ on are independently selected from one or more of $C_{1-6}$alkyl, halo, halo-substituted $C_{1-6}$alkyl, $OC_{1-6}$alkyl, halo-substituted $OC_{1-6}$alkyl, $C_{3-10}$cycloalkyl, aryl and heteroaryl, and at least one of $R^1$, $R^2$, $R^3$, $R^4$, the ring system formed by $R^1$ and $R^2$ and the ring system formed by $R^3$ and $R^4$, or a substituent thereon, comprises at least one chiral center;

X is a neutral or an anionic ligand; and n is an integer representing the number of ligands, X, to fulfill the valency requirements of N, and when x is greater than 1, each X may be the same or different.

2. The metal catalyst according to claim 1, wherein $R^1$, $R^2$, $R^3$ and $R^4$ are independently selected from $C_{1-6}$alkyl, $C_{5-6}$cycloalkyl and aryl, each group being optionally substituted, or $R^1$ and $R^2$ and/or $R^3$ and $R^4$ are linked to form, together with the nitrogen atom to which they are attached, an optionally substituted monocyclic, saturated ring system that contains 4 to 7 carbon atoms, and the optional substituents on $R^1$, $R^2$, $R^3$ and $R^4$ are independently selected from one to five of $C_{1-4}$alkyl, halo-substituted $C_{1-4}$alkyl, $C_{5-6}$cycloalkyl and aryl, and at least one of $R^1$, $R^2$, $R^3$, $R^4$, the ring system formed by $R^1$ and $R^2$ and the ring system formed by $R^3$ and $R^4$, or a substituent thereon, comprises at least one chiral center.

3. The metal catalyst according to claim 2, wherein the chiral ADC of formula II is selected from:

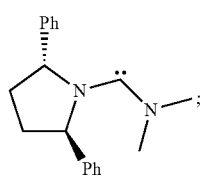

(IIa)

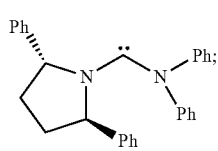

(IIb)

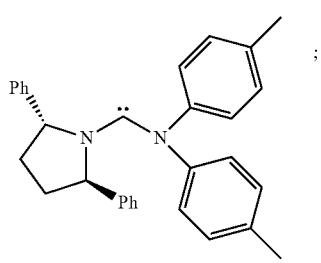

(IIc)

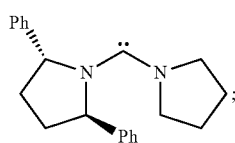

(IId)

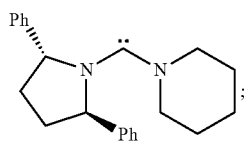

(IIe)

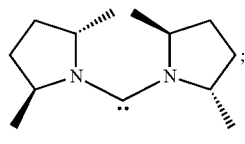

(IIIf)

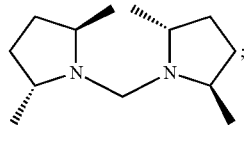

(IIg)

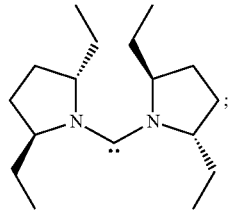

(IIh)

-continued

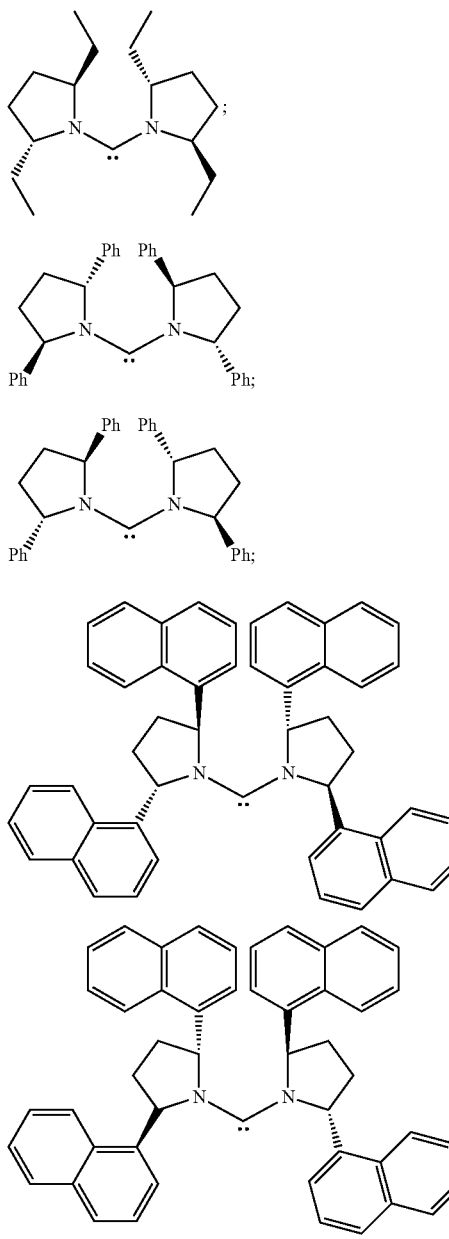

and analogs of the above compounds that are substituted on the alkyl rings, phenyl rings, aromatic and/or pyrrolidine rings with one or more substituents independently selected from $C_{1-6}$alkyl, halo, halo-substituted $C_{1-6}$alkyl, $OC_{1-6}$alkyl and halo-substituted $OC_{1-6}$alkyl.

4. The metal catalyst according to claim 1, wherein M is any transition metal, or other metal selected from B, Al, Ga, Ge, In, Sn, Sb, Tl, Pb, Bi and Po, or a lanthanide or actinide.

5. The metal catalyst according to claim 4, wherein M is selected from Cu, Ag, Au, Sn, Ni, Pd, Pt, Co, Rh, Ir, Fe, Ru, Os and Re.

6. The metal catalyst according to claim 1, wherein X is selected from any ancillary ligand, including phosphine, amine, alkene, diamine, diphosphine, aminophosphine, halo, $HO^-$, $R^5O^-$ and $R^5C(O)O^-$, wherein $R^5$ is H or $C_{1-6}$alkyl.

7. The metal catalyst according to claim 6, wherein X is chloro.

8. The metal catalyst according to claim 1, wherein when n is greater than 1, all X ligands are the same.

9. A chiral formamidium salt selected from:

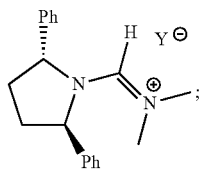

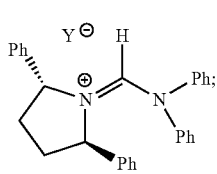

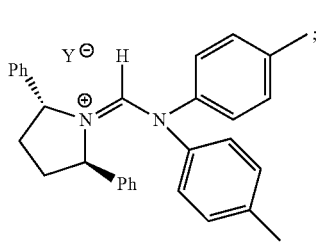

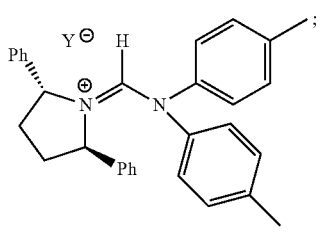

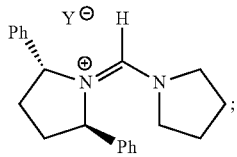

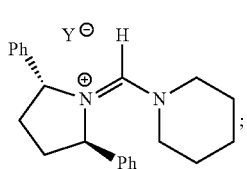

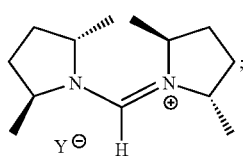

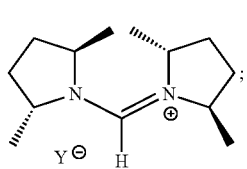

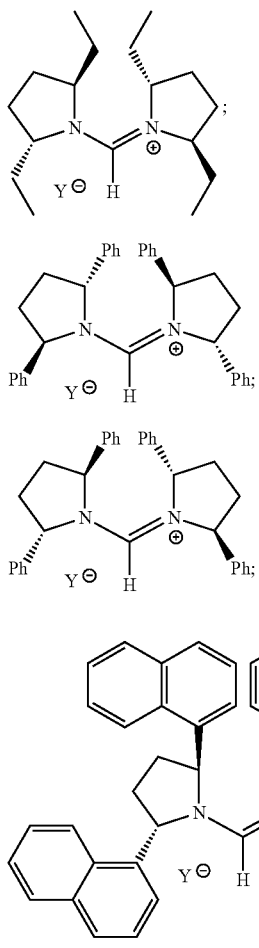

(IIIi)

(IIIj)

(IIIk)

(IIIl) and

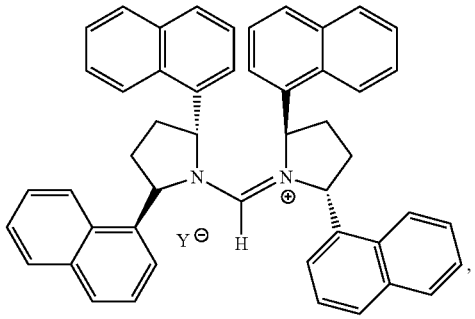

(IIIm)

where Y is a counteranion, and analogs of the above compounds that are substituted on the alkyl groups, phenyl rings, aromatic and/or pyrrolidine rings with one or more substituents independently selected from $C_{1-6}$alkyl, halo and halo-substituted $C_{1-6}$alkyl.

10. A method of performing metal-catalyzed organic synthesis reactions comprising contacting substrates for the organic synthesis reaction with a metal catalyst of the formula I as defined in claim 1 under conditions for performing the organic synthesis reaction, and optionally isolating one or more products from the organic synthesis reaction.

11. The method according to claim 10, wherein the organic synthesis reaction is selected from hydrosilations, hydrogenations, conjugate additions and cross-couplings.

12. The method according to claim 10, wherein the organic synthesis transformation is an asymmetric or chiral synthesis reaction.

* * * * *